US00RE49753E

(19) United States
(12) Reissued Patent
Suddaby et al.

(10) Patent Number: US RE49,753 E
(45) Date of Reissued Patent: Dec. 12, 2023

(54) ADJUSTABLE IMPLANT AND INSERTION TOOL

(71) Applicant: K2M, Inc., Leesburg, VA (US)

(72) Inventors: Loubert Suddaby, Orchard Park, NY (US); Larry E. McClintock, Gore, VA (US)

(73) Assignee: K2M, Inc., Leesburg, VA (US)

(21) Appl. No.: 16/676,056

(22) Filed: Nov. 6, 2019

Related U.S. Patent Documents

Reissue of:
(64) Patent No.: 9,808,353
Issued: Nov. 7, 2017
Appl. No.: 15/181,822
Filed: Jun. 14, 2016

U.S. Applications:
(62) Division of application No. 14/282,299, filed on May 20, 2014, now Pat. No. 9,393,130.
(Continued)

(51) Int. Cl.
*A61F 2/46* (2006.01)
*A61F 2/44* (2006.01)
(Continued)

(52) U.S. Cl.
CPC ..... *A61F 2/447* (2013.01); *A61F 2/4425* (2013.01); *A61F 2/46* (2013.01); *A61F 2/4611* (2013.01);
(Continued)

(58) Field of Classification Search
None
See application file for complete search history.

(56) References Cited

U.S. PATENT DOCUMENTS 5,554,191 A 9/1996 Lahille et al.
5,665,122 A 9/1997 Kambin
(Continued)

FOREIGN PATENT DOCUMENTS

FR 2 717 068 A1 9/1995
WO 2014145766 A1 9/2014
(Continued)

OTHER PUBLICATIONS

Australian Search Report for Application No. 2015330678, dated Jul. 5, 2019, p. 1.
(Continued)

*Primary Examiner* — David O Reip
(74) *Attorney, Agent, or Firm* — Lerner David LLP

(57) ABSTRACT

An adjustable spinal implant includes a lower body, an upper body, a locking pawl, and a locking key. The upper body and the lower body are pivotable relative to one another between a collapsed position and an expanded position. The upper body includes a locking flange that extends towards the lower body. The locking pawl is coupled to the lower body and is moveable between a locked position such that the upper and lower bodies are fixed relative to the one another and an unlocked position such that the upper and lower bodies are moveable relative to one another. The locking key is moveable between a locked state such that the locking pawl is fixed in the locked position and an unlocked state wherein the locking pawl is moveable between the locked position and the unlocked position.

33 Claims, 7 Drawing Sheets

Related U.S. Application Data

(60) Provisional application No. 61/825,117, filed on May 20, 2013.

(51) Int. Cl.
*A61F 2/28* (2006.01)
*A61F 2/30* (2006.01)

(52) U.S. Cl.
CPC ..... *A61F 2002/2817* (2013.01); *A61F 2002/2835* (2013.01); *A61F 2002/3054* (2013.01); *A61F 2002/30266* (2013.01); *A61F 2002/30281* (2013.01); *A61F 2002/30484* (2013.01); *A61F 2002/30522* (2013.01); *A61F 2002/30538* (2013.01); *A61F 2002/30556* (2013.01); *A61F 2002/30568* (2013.01); *A61F 2002/30593* (2013.01); *A61F 2002/30594* (2013.01); *A61F 2002/30624* (2013.01); *A61F 2002/30828* (2013.01); *A61F 2002/30831* (2013.01); *A61F 2002/448* (2013.01)

(56) References Cited

U.S. PATENT DOCUMENTS 6,102,950 A 8/2000 Vaccaro
6,159,244 A 12/2000 Suddaby
6,174,334 B1 1/2001 Suddaby
6,176,882 B1 1/2001 Biedermann et al.
6,190,414 B1 2/2001 Young et al.
6,193,757 B1 * 2/2001 Foley ..... A61F 2/4455 623/17.16
6,200,348 B1 3/2001 Biedermann et al.
6,332,895 B1 12/2001 Suddaby
6,395,031 B1 5/2002 Foley et al.
6,409,766 B1 6/2002 Brett
6,436,140 B1 8/2002 Liu et al.
6,443,989 B1 9/2002 Jackson
6,454,807 B1 9/2002 Jackson
6,491,724 B1 12/2002 Ferree
6,576,016 B1 6/2003 Hochshuler et al.
6,641,614 B1 11/2003 Wagner et al.
6,685,742 B1 2/2004 Jackson
6,709,458 B2 3/2004 Michelson
6,716,247 B2 4/2004 Michelson
6,773,460 B2 8/2004 Jackson
6,808,537 B2 10/2004 Michelson
6,814,756 B1 11/2004 Michelson
6,835,206 B2 12/2004 Jackson
6,852,129 B2 2/2005 Gerbec et al.
6,863,673 B2 3/2005 Gerbec et al.
6,962,606 B2 11/2005 Michelson
6,972,035 B2 12/2005 Michelson
7,008,453 B1 3/2006 Michelson
7,044,971 B2 5/2006 Suddaby
7,118,579 B2 10/2006 Michelson
7,211,112 B2 5/2007 Baynham et al.
7,217,291 B2 5/2007 Zucherman et al.
7,217,293 B2 5/2007 Branch, Jr.
7,588,573 B2 9/2009 Berry
7,618,458 B2 11/2009 Biedermann et al.
7,655,027 B2 2/2010 Michelson
7,678,148 B2 3/2010 Peterman
7,691,147 B2 4/2010 Gutlin et al.
7,708,779 B2 5/2010 Edie
7,722,674 B1 5/2010 Grotz
7,731,751 B2 6/2010 Butler et al.
7,771,473 B2 8/2010 Thramann
7,776,091 B2 8/2010 Mastrorio et al.
7,794,501 B2 9/2010 Edie et al.
7,799,081 B2 9/2010 McKinley
7,828,849 B2 11/2010 Lim
7,850,733 B2 12/2010 Baynham et al.
7,883,542 B2 2/2011 Zipnick
7,909,870 B2 3/2011 Kraus
7,922,729 B2 4/2011 Michelson
7,967,867 B2 6/2011 Barreiro et al.
8,062,366 B2 11/2011 Melkent
8,062,375 B2 11/2011 Glerum et al.
8,075,621 B2 12/2011 Michelson
8,097,034 B2 1/2012 Michelson
8,105,382 B2 1/2012 Olmos et al.
8,110,004 B2 2/2012 Valdevit et al.
8,118,871 B2 2/2012 Gordon et al.
8,123,810 B2 2/2012 Gordon et al.
8,133,232 B2 3/2012 Levy et al.
8,137,405 B2 3/2012 Kostuik et al.
8,147,550 B2 4/2012 Gordon et al.
8,152,851 B2 4/2012 Mueller et al.
8,152,852 B2 4/2012 Biyani
8,172,903 B2 5/2012 Gordon et al.
8,182,537 B2 5/2012 Refai et al.
8,187,331 B2 5/2012 Strohkirch, Jr. et al.
8,192,495 B2 6/2012 Simpson et al.
8,197,546 B2 6/2012 Doubler et al.
8,211,178 B2 7/2012 Melkent et al.
8,221,502 B2 7/2012 Branch, Jr.
8,231,656 B2 7/2012 Lee et al.
8,257,440 B2 9/2012 Gordon et al.
8,257,442 B2 9/2012 Edie et al.
8,273,126 B2 9/2012 Lindner
8,303,663 B2 11/2012 Jimenez et al.
8,308,802 B2 11/2012 Rhoda et al.
8,328,871 B2 12/2012 Capote et al.
8,337,558 B2 12/2012 Lindner
8,337,559 B2 12/2012 Hansell et al.
8,349,014 B2 1/2013 Barreiro et al.
8,353,961 B2 1/2013 McClintock et al.
8,366,777 B2 2/2013 Matthis et al.
8,382,842 B2 2/2013 Greenhalgh et al.
8,394,143 B2 3/2013 Grotz et al.
8,398,713 B2 3/2013 Weiman
8,425,608 B2 4/2013 Dewey et al.
8,435,296 B2 5/2013 Kadaba et al.
8,480,738 B2 7/2013 Edie et al.
8,496,706 B2 7/2013 Ragab et al.
8,512,406 B2 8/2013 White et al.
8,518,114 B2 8/2013 Marik
8,628,578 B2 1/2014 Miller et al.
8,663,329 B2 3/2014 Ernst
8,679,183 B2 3/2014 Glerum et al.
8,721,723 B2 5/2014 Hansell et al.
8,795,366 B2 8/2014 Varela
8,845,733 B2 9/2014 O'Neil et al.
8,894,711 B2 11/2014 Varela
9,034,045 B2 5/2015 Davenport et al.
9,198,769 B2 12/2015 Perrow et al.
9,271,846 B2 3/2016 Lim et al.
9,393,130 B2 7/2016 Suddaby et al.
9,572,680 B2 2/2017 Theofilos et al.
9,585,762 B2 3/2017 Suddaby et al.
9,808,352 B2 11/2017 Suddaby et al.
9,839,528 B2 12/2017 Weiman et al.
9,872,777 B2 1/2018 Ganter et al.
2002/0068976 A1 6/2002 Jackson
2002/0128712 A1 9/2002 Michelson
2002/0128713 A1 9/2002 Ferree
2002/0177897 A1 11/2002 Michelson
2004/0059421 A1 3/2004 Glenn et al.
2004/0087947 A1 5/2004 Lim et al.
2004/0249461 A1 12/2004 Ferree
2004/0254643 A1 12/2004 Jackson
2005/0015149 A1 1/2005 Michelson
2005/0125061 A1 6/2005 Zucherman et al.
2006/0030943 A1 2/2006 Peterman
2006/0122701 A1 6/2006 Kiester
2006/0167547 A1 7/2006 Suddaby
2006/0195095 A1 8/2006 Mueller et al.
2006/0200244 A1 9/2006 Assaker
2007/0016221 A1 1/2007 Beyersdorff et al.
2007/0270964 A1 11/2007 Strohkirch et al.
2008/0004705 A1 1/2008 Rogeau et al.
2008/0045968 A1 2/2008 Yu et al.
2009/0099568 A1 4/2009 Lowry et al.

(56) References Cited

U.S. PATENT DOCUMENTS

| | | | |
|---|---|---|---|
| 2009/0204215 | A1 | 8/2009 | McClintock et al. |
| 2009/0281625 | A1 | 11/2009 | Enayati |
| 2010/0057208 | A1 | 3/2010 | Dryer et al. |
| 2010/0094424 | A1 | 4/2010 | Woodburn et al. |
| 2010/0145455 | A1 | 6/2010 | Simpson et al. |
| 2010/0262247 | A1 | 10/2010 | Arnin |
| 2010/0280616 | A1 | 11/2010 | Frasier |
| 2010/0286777 | A1 | 11/2010 | Errico et al. |
| 2010/0324687 | A1 | 12/2010 | Melkent et al. |
| 2011/0172774 | A1 | 7/2011 | Varela |
| 2011/0319997 | A1 | 12/2011 | Glerum et al. |
| 2012/0029636 | A1 | 2/2012 | Ragab et al. |
| 2012/0029637 | A1 | 2/2012 | Ragab et al. |
| 2012/0185045 | A1 | 7/2012 | Morris et al. |
| 2012/0185049 | A1 | 7/2012 | Varela |
| 2012/0226357 | A1 | 9/2012 | Varela |
| 2012/0310350 | A1 | 12/2012 | Farris et al. |
| 2013/0116791 | A1 | 5/2013 | Theofilos |
| 2013/0158663 | A1 | 6/2013 | Miller et al. |
| 2013/0158664 | A1 | 6/2013 | Palmatier et al. |
| 2013/0197642 | A1 | 8/2013 | Ernst |
| 2013/0211526 | A1 | 8/2013 | Alheidt et al. |
| 2014/0188225 | A1 | 7/2014 | Dmuschewsky |
| 2014/0214166 | A1 | 7/2014 | Theofilos |
| 2014/0243982 | A1 | 8/2014 | Miller |
| 2014/0277479 | A1 | 9/2014 | Raymond et al. |
| 2014/0277502 | A1 | 9/2014 | Schiffman et al. |
| 2014/0343678 | A1 | 11/2014 | Suddaby et al. |
| 2015/0012098 | A1 | 1/2015 | Eastlack et al. |
| 2015/0057755 | A1 | 2/2015 | Suddaby et al. |
| 2015/0250609 | A1 | 9/2015 | McLean et al. |
| 2016/0022433 | A1 | 1/2016 | Davenport |
| 2016/0100951 | A1 | 4/2016 | Suddaby et al. |

FOREIGN PATENT DOCUMENTS

| | | | |
|---|---|---|---|
| WO | 2015063721 | A1 | 5/2015 |
| WO | 2016057940 | A1 | 4/2016 |

OTHER PUBLICATIONS

European Search Report dated Aug. 7, 2017 issued in corresponding European Application No. 7157602.8-1501.

International Search Report for PCT/US2015/054969 dated Jan. 8, 2016.

International Search Report dated Sep. 30, 2014 dated in PCT/US2014/038726.

International Preliminary Report on Patentability dated Nov. 24, 2015, issued in PCT/US2014/038726.

International Preliminary Report on Patentability dated Dec. 3, 2015, issued in PCT/US2014/038726.

European Search Report dated Dec. 12, 2016, issued in EP Application No. 14801054.

* cited by examiner

10

ADJUSTABLE IMPLANT AND INSERTION TOOL

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

The present application is *an application for the reissue of U.S. Pat. No. 9,808,353, which is* a divisional of U.S. patent application Ser. No. 14/282,299, filed May 20, 2014, which claims the benefit of and priority to U.S. Provisional Patent Application Ser. No. 61/825,117 filed on May 20, 2013. The entire contents of each of the above applications are incorporated herein by reference.

BACKGROUND

1. Technical Field

The present disclosure relates to a device for use in orthopedic surgeries and, more specifically, to an adjustable implant, an insertion tool for an adjustable implant, and a method for inserting an adjustable implant into an intervertebral space.

2. Discussion of Related Art

Adjustable implants may serve to stabilize adjacent vertebral elements, thereby facilitating the development of a boney union between them and thus long term spinal stability. Stresses acting upon the human backbone (or "vertebral column") may result in a variety of problems or disease states.

For example, intervertebral discs have a high propensity to degenerate. Overt or covert trauma occurring in the course of repetitive activities disproportionately affects the more highly mobile areas of the spine. Disruption of a disc's internal architecture leads to bulging, herniation, or protrusion of pieces of the disc and eventual disc space collapse. Any resulting irritation (e.g., mechanical or chemical) of surrounding neural elements (e.g., spinal cord and nerves) may cause pain that is attended by varying degrees of disability. In addition, loss of disc space height relaxes tension on the longitudinal spinal ligaments, thereby contributing to varying degrees of spinal instability such as spinal curvature.

The time-honored method according to addressing the issues of neural irritation and instability resulting from severe disc damage have largely focused on removal of the damaged disc and fusing the adjacent vertebral elements together. Removal of the disc relieves the mechanical and chemical irritation of neural elements, while osseous union (i.e., bone knitting) solves the problem of instability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term boney union occurs. For these reasons, interbody fusion using bone alone may have an unacceptable rate of bone graft migration, expulsion, or nonunion due to structural failures of the bone or residual degrees of motion that retard or prohibit boney union. Intervertebral prostheses in various forms have therefore been used to provide immediate stability and to protect and preserve an environment that fosters growth of grafted bone such that a structurally significant boney fusion can occur.

Limitations of present-day intervertebral implants can be significant and revolve largely around the marked variation in disc space shape and height which results from either biologic variability or pathologic change. For example, if a disc space is 20 mm in height, a circular implant bridging this gap requires a minimum height of 20 mm just to contact the end plate of the vertebral bone. Generally, end plate disruption must occur to allow a generous boney union, meaning that an additional 2-3 mm must be added on either end, resulting in a final implant size of 24-26 mm. During implantation from an anterior approach (i.e., from the front of the body), excessive retraction (i.e., pulling) is often required on the great blood vessels which may damage the great blood vessels resulting in vascular tears or thrombosis. On the other hand, during a posterior approach, large implant diameters may require excessive traction on neural elements for adequate placement, even if all posterior boney elements are removed. In some instances, an adequate implant size cannot be inserted posteriorly, particularly if there is a significant degree of ligamentous laxity requiring higher degrees of distraction to obtain stability by tightening the annular ligamentous tension band. Compromising on implant size risks sub-optimal stability or a loose implant, which has a greater chance for migration within or expulsion from the disc space. The alternative of excessively retracting neural elements to facilitate a posterior implant application may result damage to the neural elements.

Therefore, a need exists for an adjustable implant that can be inserted in a collapsed position in order to prevent over retraction of the anatomy or substandard implant sizing and once the implant is in place be expanded to fill the anatomical space appropriately.

SUMMARY

In an aspect of the present disclosure, an adjustable spinal implant includes a lower body, an upper body, a locking pawl, and a locking key. The upper and lower bodies are pivotally moveable relative to one another between a collapsed position and an expanded position. The upper body includes a locking flange extending towards the lower body. The locking pawl is coupled to the lower body and is moveable between a locked position and an unlocked position. In the locked position, the upper and lower bodies are fixed relative to one another. In the unlocked position, the upper and lower bodies are pivotable relative to one another. The locking flange may extend adjacent a distal end of the upper body.

In aspects, locking flange defines a locking slot that receives a portion of the locking key. The locking key may include a distal ball that is received within the locking slot to fix the locking key in the locked position. The locking pawl may define an opening that receives the locking key therethrough.

In some aspects, the locking key includes a keyed ring that abuts a proximal face of the locking pawl to prevent the locking key from passing through the opening. The locking key may be rotatable within the opening between a first radial position, such that the locking key is in the locked state, and a second radial position, such that the locking key is in the unlocked state. The keyed ring may define a key slot in a circumference thereof that limits the rotation of the locking key within the opening between the first and second radial positions.

In particular aspects, the locking key includes a retention ring that is positioned distal to the keyed ring. The locking pawl may define a transverse passage that is in communication with the opening. The locking pawl may include a retention pin that is received within the transverse passage which engages the retention ring to prevent the retention ring from passing through the locking pawl.

In certain aspects, the implant includes biasing members that urge the locking pawl towards the locked position. The biasing members may be secured relative to a surface of the lower body opposing the upper body and the locking pawl may include biasing fingers that extend from a proximal face thereof that are positioned over the biasing members.

In aspects, the lower body includes lower sidewalls that extend towards the upper body and the upper body includes upper sidewalls that extend towards the lower body. The lower sidewalls may engage the upper sidewalls when the implant is in the collapsed position and the lower sidewall may be spaced apart from the upper sidewalls when the implant is in the expanded position.

In some aspects, a proximal face of the locking flange includes teeth and a distal face of the locking pawl includes teeth opposing the teeth of the locking flange. In the locked state of the locking key the teeth of the locking flange and the teeth of the locking pawl are engaged with each other to prevent the upper and lower bodies from moving relative to one another and in the unlocked state of the locking key the teeth of the locking flange may be slidable over the teeth of the locking pawl to permit the upper and lower bodies to move relative to one another. In the unlocked state of the locking key, the upper and lower bodies may be moveable away from one another. In the unlocked state of the locking key, the upper and lower bodies may be prevented from moving towards one another.

In another aspect of the present disclosure, an implant insertion tool includes a locking rod, a spreading rod, an upper section, a lower section, and a thumb wheel. The spreading rod includes proximal and distal ends and an elongate body therebetween. The upper section defines an upper channel that receives a portion of the locking rod. The lower section includes a proximal portion, an elongate portion extending from the proximal portion, and a distal portion. The elongate and distal portions define a lower channel that receives a portion of the spreading rod therein. The thumb wheel is disposed over the elongate portion of the lower section and is engaged with the proximal end of the spreading rod.

In aspects, the spreading rod includes a rod guide that is positioned adjacent the distal end thereof. The rod guide may define a rod passage that receives a portion of the locking rod therethrough. The thumb wheel may define a threaded passage that is threadably engaged with the proximal end of the spreading rod such that the rotation of the thumb wheel longitudinally translates the spreading rod within the lower channel.

In some aspects, the upper section defines a locking recess in an outer surface thereof that is in communication with the upper channel. The locking recess may include a proximal transport portion, a distal locking portion, and an engagement portion therebetween. The locking rod may include a proximal engagement end that is disposed in the locking recess formed in the upper section. The proximal engagement end may extend orthogonal to a longitudinal axis defined by the lower portion. The locking rod may include a distal end that is extendable beyond the distal end of the spreading rod. The distal end of the locking rod may be configured to engage a locking key of an implant to transition the locking key between locked and unlocked states.

In particular aspects, the tool includes a cap that defines a threaded hole. The threaded hole may engage the proximal portion of the lower section to retain the thumb wheel over the elongate portion of the lower section.

In yet another aspect of the present disclosure, a method according to expanding an implant includes positioning an adjustable implant in an intervertebral space, pivoting a distal end of the upper body and a distal end of the lower body away from one another, and transitioning a locking key to a locked state. The adjustable implant may be any of the adjustable implants disclosed herein. The locking pawl may ratchet between locked and unlocked positions as the upper and lower bodies pivot away from one another. Transitioning the locking key to the locked state includes fixing the locking pawl in the locked position to fix the upper and lower bodies relative to one another.

In aspects, pivoting the distal ends of the upper and lower bodies away from one another includes inserting an insertion tool in a passage defined by the upper and lower bodies. The insertion tool may be any of the insertion tools disclosed herein.

In some aspects, the method includes capturing a portion of the lower body within a cutout defined in a distal portion of the insertion tool such that the implant is longitudinally fixed relative to the insertion tool. The method may include translating a spreading rod of the insertion tool into the passages to pivot the distal ends of the upper and lower bodies away from one another. Translating the spreading rod may include engaging the upper body with a rod guide to pivot the distal ends of the upper and lower bodies away from one another. Translating the spreading rod may include rotating a thumb wheel that is threadably coupled to a proximal end of the spreading rod.

In particular aspects, translating the locking key to the locked state includes rotating the locking key. The method may include engaging the locking key with a locking rod of an insertion tool. Transitioning the locking key to the locked state may include rotating the locking rod to rotate the locking key. Engaging the locking key may include receiving a proximal end of the locking key in a recess defined in a distal end of the locking rod.

In certain aspects, engaging the locking key includes rotating a proximal engagement end of the locking rod that is disposed within a transport portion of a locking recess defined in an upper section of the insertion tool in a first radial direction and sliding the proximal engagement end of the locking rod within an engagement portion of the locking recess until the locking rod is engaged with the locking key. The engagement portion may be positioned distal to the transport portion. Transitioning the locking key to the locked state may include rotating the locking rod within a locking portion of the locking recess in the first radial direction. The locking portion may be positioned distal to the engagement portion. The method may include disengaging the locking rod from the proximal end of the locking key by translating the proximal engagement portion proximally within the locking portion of the locking recess.

In aspects, the method includes limiting the rotation of the locking key with a keyed ring of the locking key engaging a stop pin that is coupled to the locking pawl.

In still another aspect of the present disclosure, a system for stabilizing adjacent vertebral elements includes an adjustable spinal implant and an insertion tool. The adjustable spinal implant may be any of the adjustable spinal implants disclosed herein and the insertion tool may be any of the insertion tools disclosed herein.

In another aspect of the present disclosure, a kit includes an adjustable spinal implant and an insertion tool. The adjustable spinal implant may be any of the adjustable spinal implants disclosed herein and the insertion tool may be any of the insertion tools disclosed herein.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
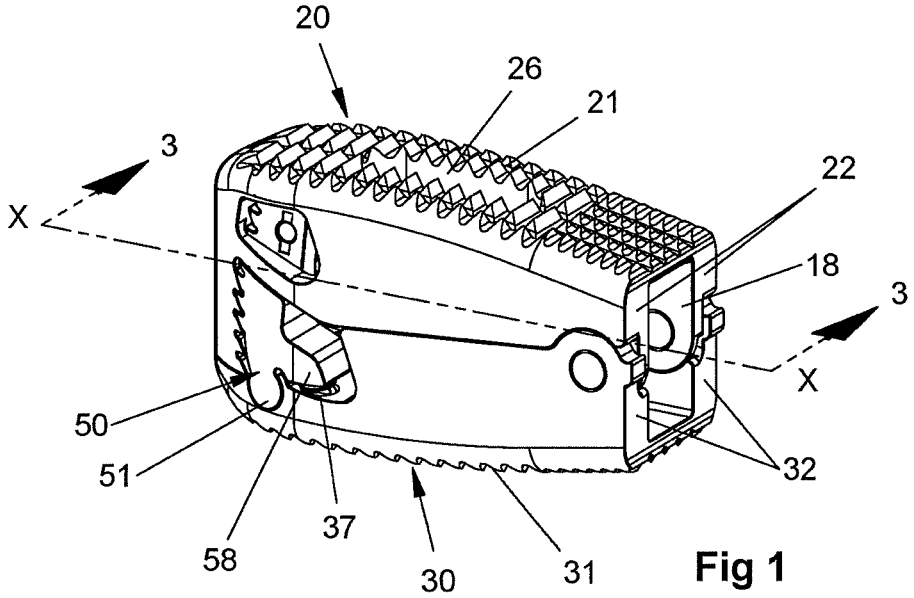
FIG. 1 is a perspective view of an exemplary implant provided in accordance with the present disclosure in a collapsed position.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. In addition, the term "cephalad" is used in this application to indicate a direction toward a patient's head, whereas the term "caudad" indicates a direction toward the patient's feet. Further still, for the purposes of this application, the term "lateral" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure.

Figure 7:
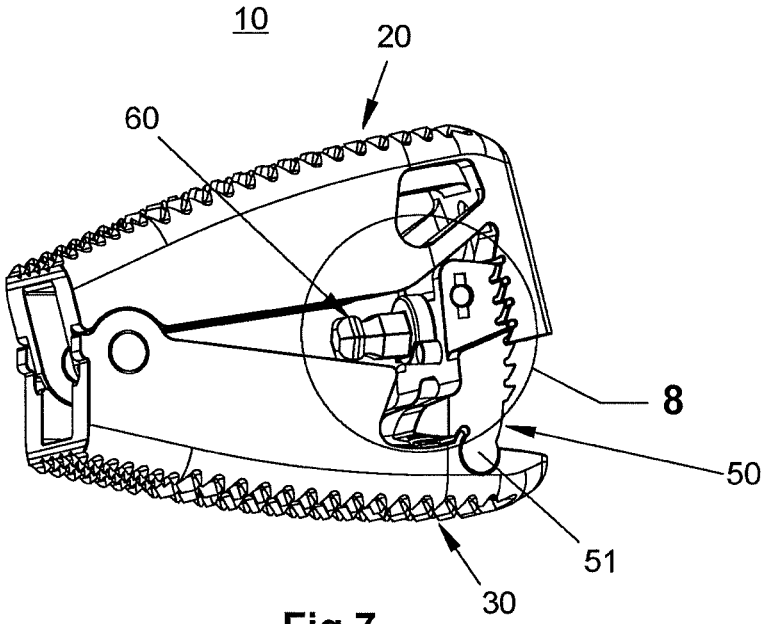
FIG. 7 is a perspective view of the implant of FIG. 1 in an expanded position with the locking key in a locked state.
Figure 8:
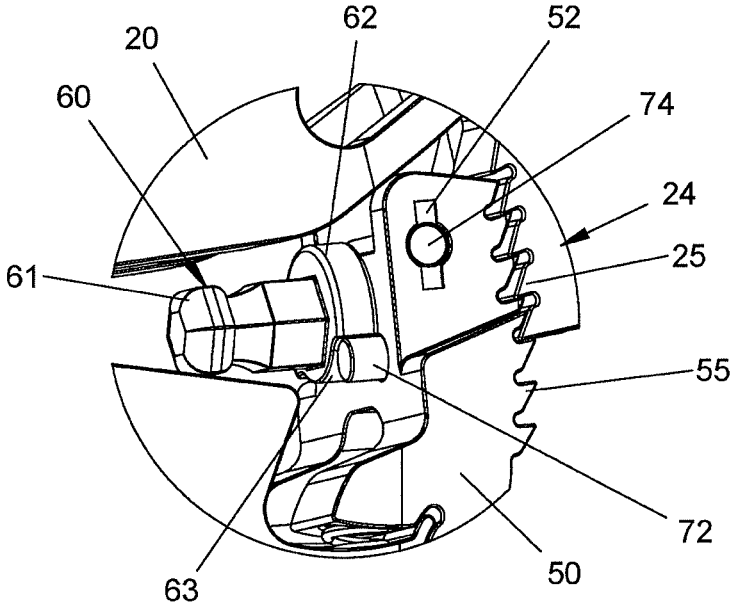
FIG. 8 is an enlarged view of the area of detail of FIG. 7.

Referring to FIG. 1, an exemplary embodiment of an adjustable spinal implant 10 in accordance with the present disclosure includes an upper body 20 and a lower body 30. The spinal implant 10 has a collapsed position (FIG. 1) where a distal end of the upper body 20 is adjacent a distal end of the lower body 30 thereby facilitating insertion of the spinal implant 10 into an intervertebral space. Once the spinal implant 10 is positioned within the intervertebral space, the spinal implant 10 is adjusted and locked in an expanded position (FIG. 7) where the distal end of the upper body 20 is spaced-apart from the distal end of the lower body 30. The upper and lower surfaces 21, 31 may be arcuate between the proximal and distal ends of the upper and lower body 20, 30, respectively. It will be appreciated that in the collapsed position, an upper surface 21 of the upper body 20 may be substantially parallel to a lower surface 31 of the lower body 30 and in the expanded position, the upper surface 21 of the upper body 20 and the lower surface 31 of the lower body 30 are disposed at an angle relative one another.

Figure 2:
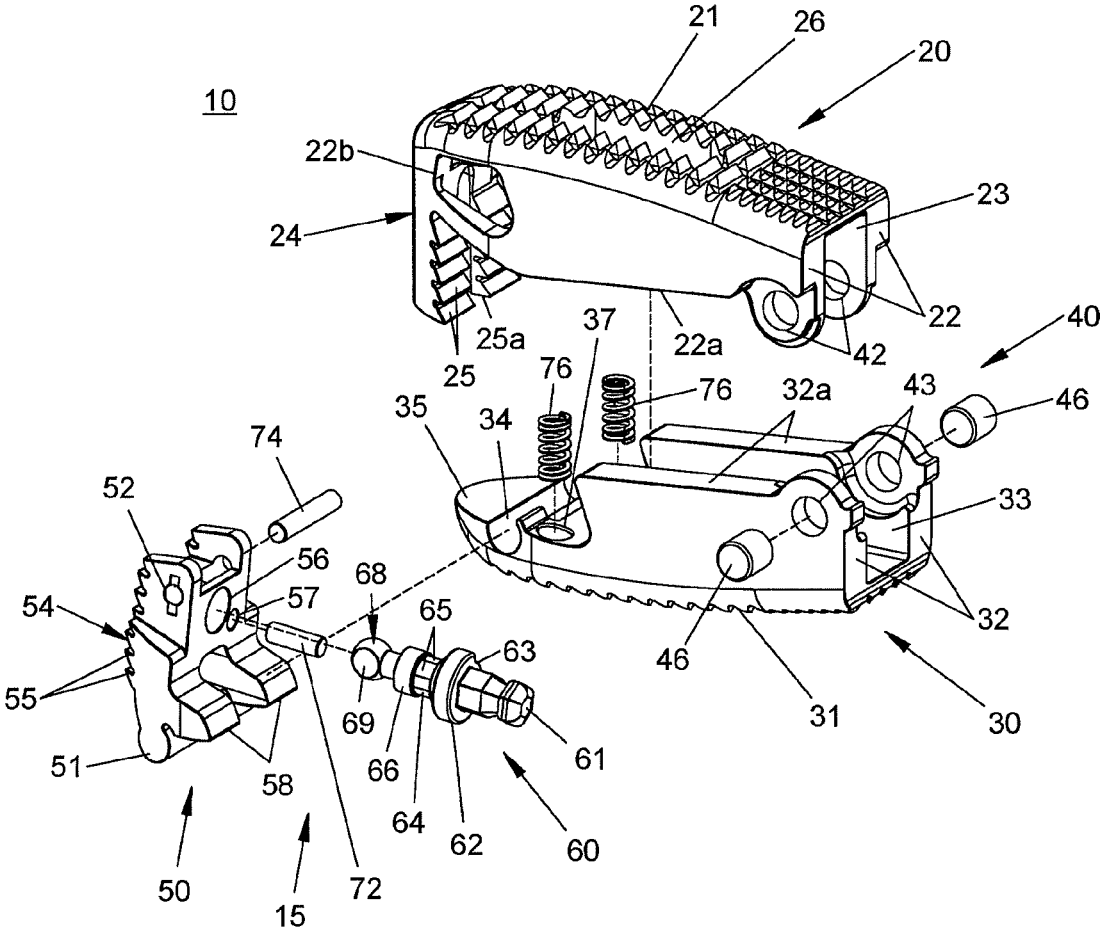
FIG. 2 is an exploded perspective view of the implant of FIG. 1 with the parts thereof separated.

The implant 10 defines a central longitudinal axis X-X and includes the upper body 20, the lower body 30, and a locking assembly 15 having a locking pawl 50 and a locking key 60 (FIG. 2). The upper and lower surfaces 21, 31 may include multiple engagement features, guiding features, or textured surface features that assist in the placement or securement of the implant 10 within an intervertebral space. The upper and lower surfaces 21, 31 may be substantially similar to one another or each of the surfaces 21, 31 may be unique. The upper and lower surfaces 21, 31 may define vertical openings 26, 36 therethrough. The features of the surfaces 21, 31 or the vertical openings 26, 36 may promote bone growth to and/or through the implant 10. The space between the vertical openings 26, 36 may be used for holding bone growth facilitators such as osteoconductive or osteoinductive materials (e.g. bone, bone chips, bone substitutes, bone growth promoting materials such as bone morphogenic proteins, etc.), or both, to enable and/or promote growth of vertebral bone therebetween to anchor the spinal implant 10 within the intervertebral space.

With additional reference to FIG. 2, the upper body 20 includes sidewalls 22 extending from the upper surface 21 towards the central longitudinal axis X-X to a lower surface 22a thereof. The lower surfaces 22a define a plane with the central longitudinal axis X-X when the implant 10 is in the collapsed position. The sidewalls 22 define a longitudinal passage 23 therebetween. Each of the sidewalls 22 define upper hinge passages 42 adjacent a proximal end thereof. Each of the sidewalls 22 may define side openings 22b that extend through the upper body 20 adjacent a distal end of the upper body 20 transverse to the central longitudinal axis X-X. Each of the sidewalls 22 may also define an angled surface 27 (FIG. 3) in an inner surface thereof.

In addition, the upper body 20 includes a locking flange 24 extending towards and/or through the central longitudinal axis X-X (i.e., downward as shown in FIG. 2) from a distal end of the upper surface 21. The locking flange 24 includes teeth 25 and defines a locking slot 25a. The teeth 25 of the locking flange 24 secure the upper body 20 relative to the lower body 30 in a plurality of positions between the collapsed and expanded positions as detailed below. The locking slot 25a is substantially cylindrical in shape and is configured to receive a portion of the locking assembly 15 as detailed below.

The lower body 30 includes sidewalls 32 extending from the lower surface 31 towards the central longitudinal axis X-X to an upper surface 32a thereof. The upper surfaces 32a define a plane with the central longitudinal axis X-X when the implant 10 is in the collapsed position. In addition, the plane defined by the lower surfaces 22a of the upper body 20 is a common plane with the plane defined by the upper surfaces 32a of the lower body 30 such that the surfaces 22a, 32a are in contact with one another when the implant 10 is in the collapsed position. The sidewalls 32 define a longitudinal passage 33 therebetween. Each of the sidewalls 32 defines a lower hinge passage 43 adjacent a proximal end thereof.

In addition, the lower body 30 defines a transverse groove 34 adjacent a distal end thereof in a surface 35 opposing the upper body 20. The transverse groove 34 defines a cylindrical profile that is transverse to the central longitudinal axis X-X. The lower body 30 may define cylindrical openings 37 that extend into the surface 35. The cylindrical openings 37 are positioned proximal to the transverse groove 34. The cylindrical openings 37 may be positioned distal to the sidewalls 32.

With continued reference to FIG. 2, the implant 10 includes a hinge assembly 40 that pivotally secures the upper body 20 to the lower body 30. The hinge assembly 40 includes hinge pins 46 that are received within the upper hinge passages 42 and the lower hinge passages 43 adjacent the proximal end of the implant 10. The hinge pins 46 are positioned along an axis orthogonal to and passing through the central longitudinal axis X-X. When the upper and lower bodies 20, 30 are pivotally secured together, the sidewalls 22, 32 define a proximal opening 18 (FIG. 1) of the implant 10.

The locking pawl 50 is positioned adjacent the distal end of the implant 10 to secure the upper body 20 relative to the lower body 30 in a plurality of pivotal positions between the collapsed position and the expanded position. The locking pawl 50 includes a pivoting feature 51 on the bottom surface thereof. The pivoting feature 51 defines an axis transverse to the central longitudinal axis X-X and is received within the transverse groove 34 of the lower body 30. The pivoting feature 51 may define a substantially cylindrical shape to permit proximal and distal pivoting of the locking pawl 50 relative to the lower body 30. The locking pawl 50 includes a toothed face or surface 54 that opposes the teeth 25 of the locking flange 24 of the upper body 20. The toothed surface 54 includes teeth 55 that engage the teeth 25 of the locking flange 24 to fix the upper body 20 relative to the lower body 30 in a plurality of positions between the collapsed and expanded position as detailed below.

Figure 6:
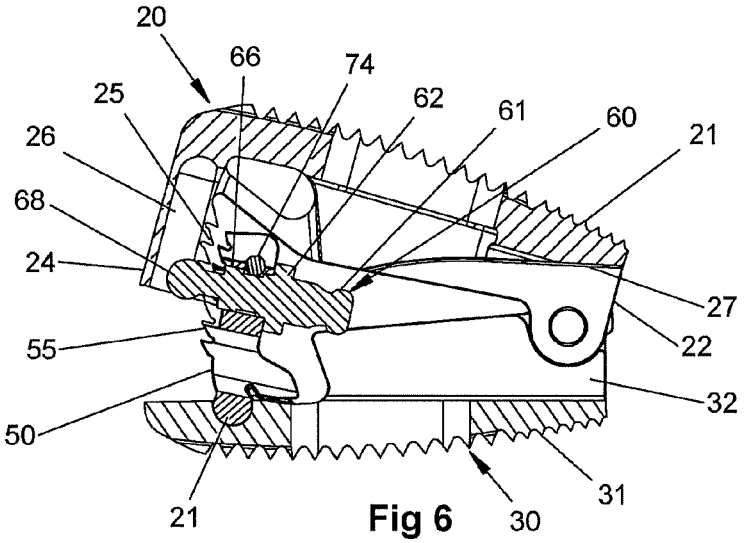
FIG. 6 is a side cross-sectional view of the implant of FIG. 4.

The pivoting feature 51 couples the locking pawl 50 to the lower body 30 and allows the locking pawl 50 to pivot between a locked position (FIG. 3) and an unlocked position (FIG. 6). In the locked position, the locking pawl 50 is pivoted towards the locking flange 24 such that the teeth 55 of the locking pawl 50 engage the teeth 25 of the locking flange 24. In the unlocked position, the locking pawl is pivoted away from the locking flange 24 such that the teeth 55 of the locking pawl 50 are spaced apart from the teeth 25 of the locking flange to permit pivotable movement of the upper body 20 and the lower body 30 away from each other as detailed below. It is contemplated that the teeth 55 of the locking pawl 50 may ratchet across the teeth 25 of the locking flange 24 as the upper body 20 and the lower body 30 pivot away from each other. In addition, it is contemplated that the teeth 55 and the teeth 25 may be shaped such that the upper body 20 and the lower body 30 may pivot away from each other and be prevented from pivoting towards each other.

Figure 3:
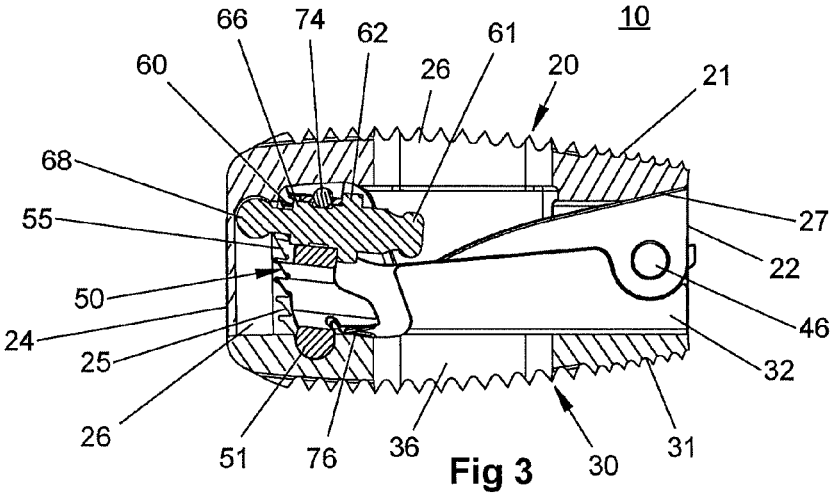
FIG. 3 is a side cross-sectional view taken along the section line 3-3 of FIG. 1.

The locking pawl 50 defines a central opening 56 therethrough defined along the central longitudinal axis X-X and an offset opening 57 adjacent the central opening 56. The central opening 56 defines an axis substantially parallel to an axis defined by the offset opening 57. The locking pawl 50 may define a transverse passage 52 adjacent the upper end (as shown in FIG. 2) of the locking pawl 50. The transverse passage 52 is in communication with the central opening 56 (FIG. 3). The locking pawl 50 includes biasing fingers 58 extending from a proximal surface of the locking pawl 50 such that when the locking pawl 50 is received within the transverse groove 34 the biasing fingers 58 are positioned over the cylindrical openings 37 (FIG. 1).

The locking assembly 15 includes biasing members 76 disposed within the cylindrical openings 37 formed in the lower body 30. The biasing members 76 engage the biasing fingers 58 of the locking pawl 50 to bias the locking pawl 50 distally towards the locked position.

Figure 5:
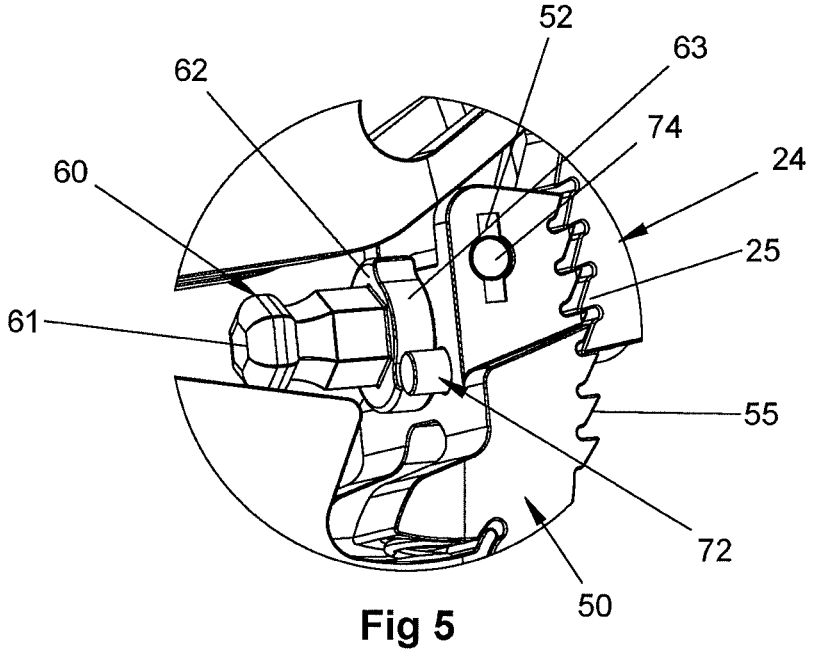
FIG. 5 is an enlarged view of the area of detail of FIG. 4.

Continuing to refer to FIG. 2, the locking assembly 15 includes a locking key 60 having, from the proximal end to the distal end thereof, a proximal end 61, a keyed ring 62, a tactile ring 64, a retention ring 66, and a distal ball 68. The proximal end 61 defines a hexagonal shape that is engagable to rotate the locking key 60 as detailed below; however, it is contemplated that the proximal end 61 may define other shapes that are engagable to rotate the locking key 60 as detailed below. The keyed ring 62 defines a keyed slot 63 (FIG. 5) in a circumference thereof. The locking assembly 15 includes a stop pin 72 received within the offset opening 57 formed in the locking pawl 50 and within the keyed slot 63 formed in the keyed ring 62 (FIG. 5) to limit the rotation of the locking key 60. The keyed slot 63 is radially disposed in about 90° of an outer radial surface of the keyed ring 62 to permit about a quarter-turn of the locking key 60; however, it is contemplated that the keyed slot 63 may be radially disposed greater or lesser than 90° in the outer radial surface of the keyed ring 62.

With additional reference to FIG. 3, the locking assembly 15 includes a retention pin 74 received within the transverse passage 52 of the locking pawl 50 to retain the locking key 60 within the central opening 56 of the locking pawl 50. Specifically, when the locking key 60 is received within the central opening 56 of the locking pawl 50, the keyed ring 62 abuts the proximal surface of the locking pawl 50 and the retention ring 66 abuts a distal surface of the retention pin 74 to retain the locking key 60 within the central opening 56.

When the locking key 60 is retained within the central opening 56, the tactile ring 64 is positioned within the central opening 56 and is aligned with the transverse passage 52. The tactile ring 64 may contact the retention pin 74 as the locking key 60 is rotated within the central opening 56. The tactile ring 64 may include surface features (e.g., flats 65 (FIG. 2)) that provide tactile feedback to a clinician as the locking key 60 is rotated within the central opening 56.

Figure 9:
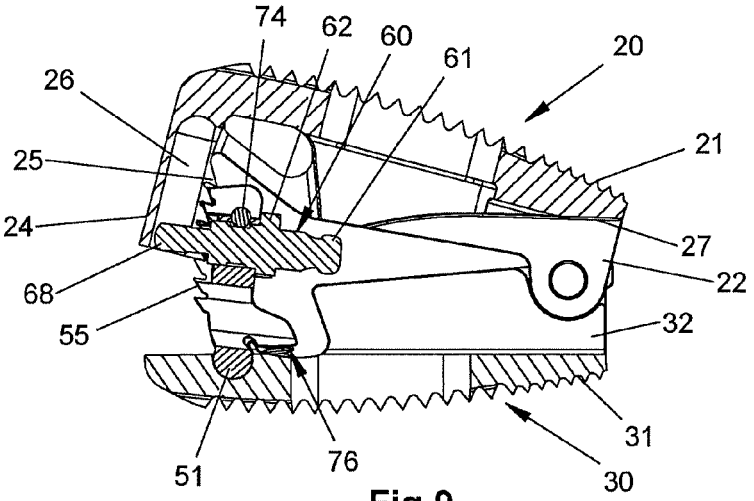
FIG. 9 is a side cross-sectional view of the implant of FIG. 7.
Figure 4:
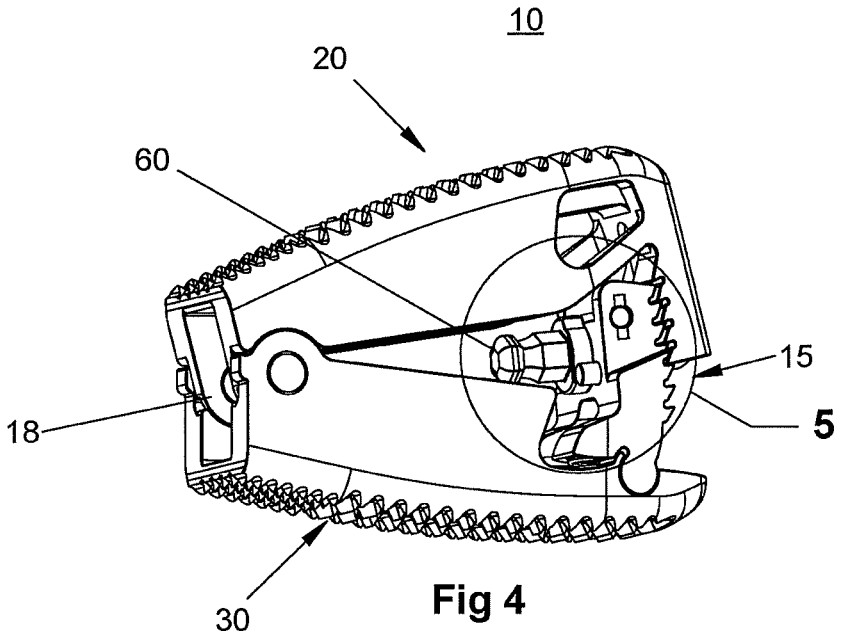
FIG. 4 is another perspective view of the implant of FIG. 1 in an expanded position with a locking key in an unlocked state.

The distal ball 68 is disposed within the locking slot 25a formed in the locking flange 24 of the upper body 20 to selectively fix the locking pawl 50 in the locked position. The distal ball 68 includes opposing ball flats 69 with arcuate surfaces therebetween that reduce an outer dimension of the distal ball 68. In an unlocked state of the locking key 60 (FIG. 3), the opposing ball flats 69 are vertically disposed within the locking slot 25a to reduce an effective outer dimension of distal ball 68 relative to the locking slot 25a such that the locking pawl 50 is allowed to move proximally against the biasing members 76, i.e., away from the locking flange 24, to its unlocked position (FIG. 6). In a locked state of the locking key 60 (FIG. 9), the opposing ball flats 69 are horizontally disposed within the locking slot 25a such that the locking pawl 50 is fixed in its locked position, i.e., the teeth 55 of the locking pawl 50 engaged with the teeth 25 of the locking flange 24. The locking slot 25a may include curved edges that engage proximal surfaces of the distal ball 68 in the locked state of the locking key 60 to prevent the distal ball 68 from moving proximally relative to the locking flange 24, i.e., out of the locking slot 25a. It will be appreciated that as the locking key 60 is rotated to transition from its unlocked state to its locked state, the proximal surfaces of the distal ball 68 may engage the locking slot 25a to move the locking pawl 50 distally and into its locked position.

Figure 10:
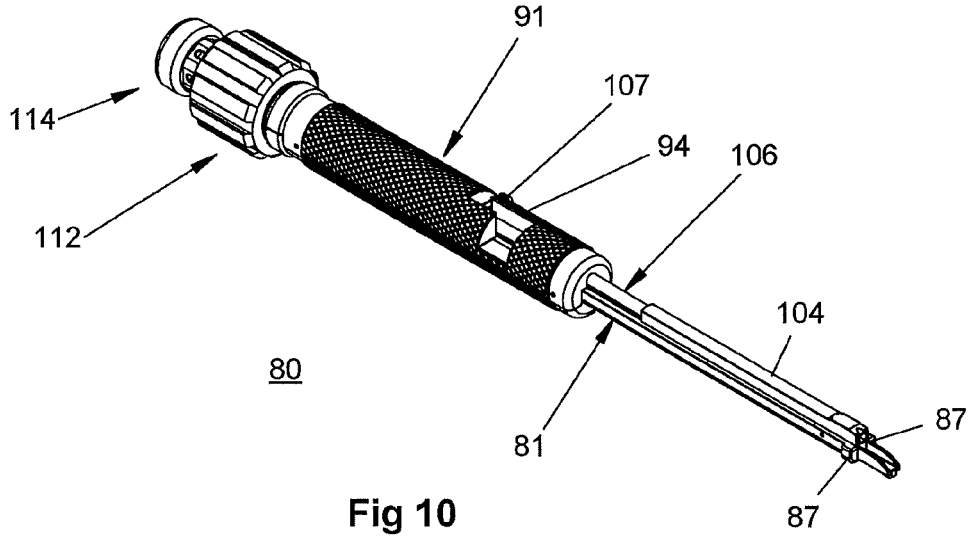
FIG. 10 is a perspective view of an exemplary insertion tool provided in accordance with the present disclosure.
Figure 11:
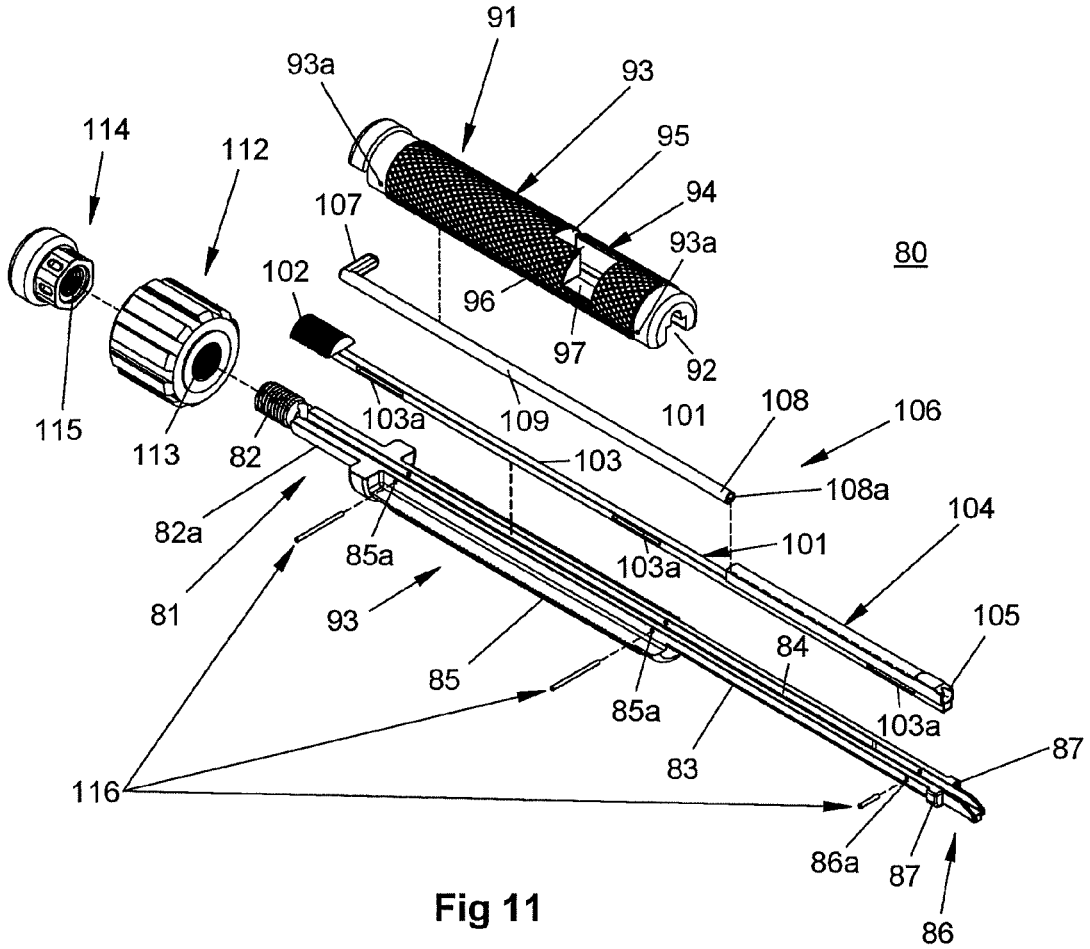
FIG. 11 is an exploded perspective view of the insertion tool of FIG. 10 with the parts thereof separated.

Referring to FIGS. 10 and 11, an exemplary embodiment of an implant insertion tool 80 is provided in accordance with the present disclosure for inserting, spreading or expanding, and locking a spinal implant (e.g., implant 10). The insertion tool 80 includes a lower section 81, an upper section 91, a spreading rod 101, a locking rod 106, a thumb wheel 112, and a cap 114.

Figure 12A:
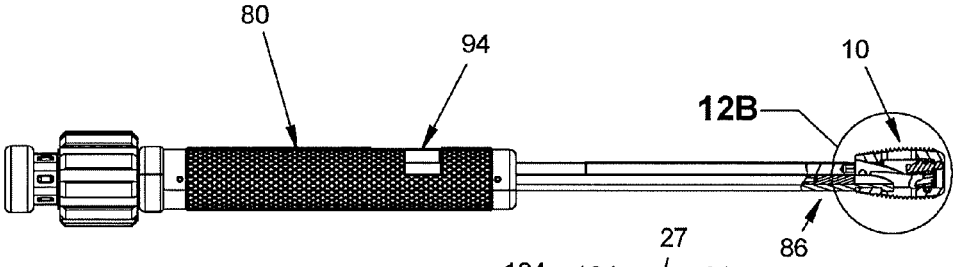
FIGS. 12A, 13A, and 14A are a progression of side views of the insertion tool of FIG. 10 with a portion of a distal end thereof cutaway and engaged with an exemplary implant to transition the implant from an unlocked collapsed position to a locked expanded position.
Figure 12B:
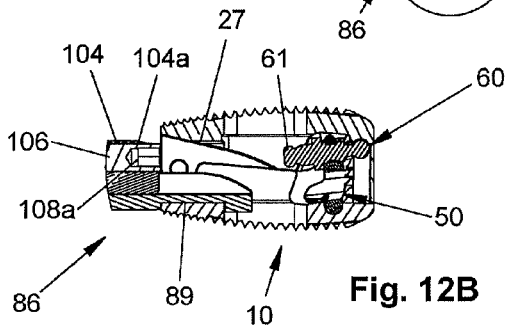
FIGS. 12B, 13B, and 14B are enlarged views of the areas of detail of FIGS. 12A, 13A, and 14A respectively.

The lower section 81 includes a proximal threaded portion 82 and an elongate portion 83 extending therefrom to a distal portion 86. The elongate portion 83 defines a lower channel 84 therealong. The elongate portion 83 includes a lower handle portion 85 disposed thereabout. The lower handle portion 85 is distal to the proximal threaded portion 82. The elongate portion 83 includes a thumb wheel race 82a positioned between the proximal threaded portion 82 and the lower handle portion 85 that rotatably receives the thumb wheel 112 as detailed below. The distal portion 86 includes abutment tabs 87 that engage proximal surfaces of a spinal implant (e.g., implant 10) as detailed below. The distal portion 86 defines an undercut 89 (FIG. 12B) in a lower surface thereof.

The upper section 91 defines an upper channel 92 therethrough and includes an upper handle portion 93. The upper section 91 is fixed to the lower section 81 as detailed below. The upper handle portion 93 defines a locking recess 94 in an upper surface thereof that includes, from a proximal to a distal end thereof, a transport portion 95, an engagement portion 96, and a locking portion 97.

The spreading rod 101 is slidably received within the lower channel 84 of the lower section 81. The spreading rod 101 includes a proximal threaded end 102 and an elongate body 103 extending therefrom. The elongate body 103 may be slidably received within the upper channel 92 of the upper section 91. The elongate body 103 defines pin slots 103a for slidably securing the elongate body 103 within the lower channel 84 of the lower section 81. The spreading rod 101 includes a rod guide 104 positioned adjacent a distal end of the elongate body 103 and is fixed to an upper surface of the elongate body 103. The rod guide 104 defines a rod passage 105 therethrough and may include a ramp 104a (FIG. 12B) positioned at a distal end thereof.

Figure 13A:
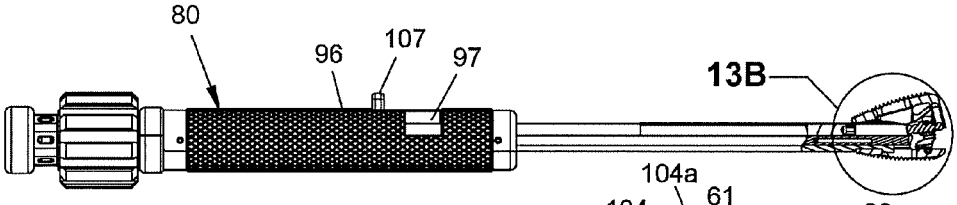
Figure 14A:
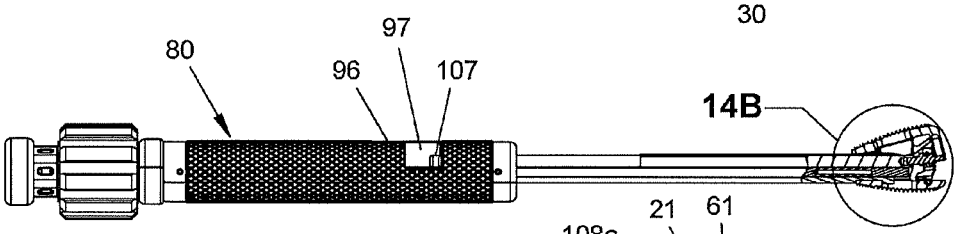
Figure 14B:
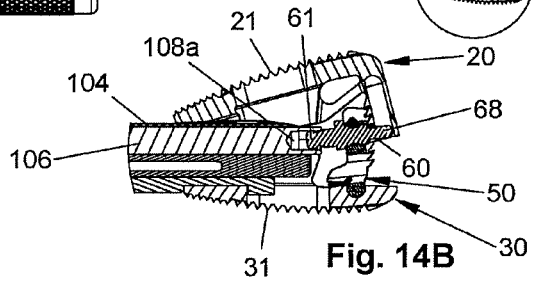

When the spreading rod 101 is received within the lower channel 84, the rod guide 104 is positioned distal to the upper section 91 and may be sized to prevent the rod guide 104 from sliding into the upper channel 92 of the upper section 91. The spreading rod 101 has a retracted position (FIGS. 10 and 12A) wherein distal end of the rod guide 104 is positioned proximal to the abutment tabs 87 of the lower section 81 and an extended position (FIG. 13A) such that the distal end of the rod guide 104 extends past the distal portion 86 of the lower body 81. The locking rod 106 includes a proximal engagement end 107, a distal end 108, and a rod portion 109 therebetween. The engagement end 107 of the locking rod 106 extends orthogonal to an axis defined by the rod portion 109. The distal end 108 of the locking rod 106 includes a recess 108a (FIG. 14B) that receives a proximal end of a locking key (e.g., proximal end 61 of locking key 60) as detailed below.

Figure 13B:
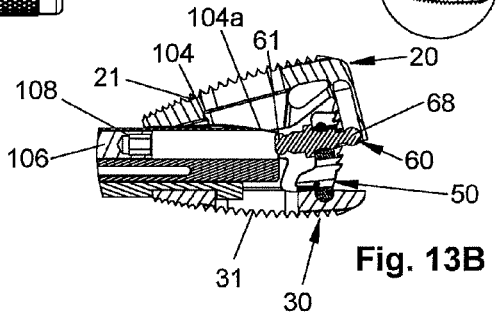

With continued reference to FIGS. 10 and 11, the thumb wheel 112 is rotatable about the thumb wheel race 82a of the lower section 81 to translate the spreading rod 101 between the retracted (FIG. 12B) and extended positions (FIG. 13B). The thumb wheel 112 defines a threaded passage 113 that threadably engages the proximal threaded end 102 of the spreading rod 101 to translate the spreading rod. The cap 114 defines a threaded hole 115 that threadably engages the proximal threaded portion 82 of the lower section 81 to longitudinally fix the thumb wheel 112 over the thumb wheel race 82a of the lower section 81. As the thumb wheel 112 is rotated about the lower section 81, the threaded passage 113 engages the proximal threaded portion 102 of the spreading rod 101 to longitudinally translate the spreading rod 101 within the lower channel 84 of the lower section 81.

To assemble the implant insertion tool 80, the elongate body 103 of the spreading rod 101 is positioned in the lower channel 84 of the lower section 81 with the proximal threaded portion 102 of the spreading rod 101 distal to the proximal threaded portion 82 of the lower section 81. The distal end 108 of the locking rod 106 is passed into the rod passage 105 of the rod guide 104. The upper section 91 is aligned with the lower section 81 with the engagement end 107 of the locking rod 106 positioned in the locking recess 94, the rod portion 109 received within the upper channel 92, and the elongate body 103 received within the upper channel 92. The lower handle portion 85 and the upper handle portion 93 are aligned to form a handle and are secured together with pins 116 passing through pin holes 93a defined in the upper handle portion 93, pin holes 85a in the lower handle portion 85, and the pin slots 103a of the elongate body 103. Another pin 116 may be inserted through a pin hole 86a in the distal portion 86 of the lower section 81 and a pin slot 103a adjacent a distal end of the spreading rod 101 to further retain the spreading rod 101 to the lower section 81. The threaded passage 113 of the thumb wheel 112 is positioned over the thumb wheel race 82a of the lower section 81 by passing over the proximal threaded portion 82 of the lower section 81 and being threaded onto the proximal threaded end 102 of the spreading rod 101. The threaded hole 115 of the cap 114 is threaded onto proximal threaded portion 82 of the lower section 81 to longitudinally fix the thumb wheel 112 over the thumb wheel race 82a between the cap 114 and a handle formed by the upper and lower handle portions 85, 93.

With reference to FIGS. 1 and 10, a system for stabilizing adjacent vertebral elements in accordance with the present disclosure includes an adjustable implant and an insertion tool. The adjustable implant of the system may be any of the adjustable implants disclosed herein (e.g., implant 10) and the insertion tool of the kit may be any of the insertion tools disclosed herein (e.g., insertion tool 80).

Referring now to FIGS. 12A-14B, a method according to inserting and expanding a spinal implant into an intervertebral space with an insertion tool is detailed below in accordance with the present disclosure. The method is detailed below using implant 10 and insertion tool 80; however, it is contemplated that the method may be performed with other implants and insertion tools.

The implant 10 is provided in the collapsed position (FIG. 12A) with the locking pawl 50 in the locked position. The insertion tool 80 is provided with the spreading rod 101 in the retracted position and the engagement end 107 of the locking rod 106 disposed in the transport portion 95 of the locking recess 94 in a transport position.

The distal portion 86 of the lower body 81 of the insertion tool 80 is inserted through the proximal opening 18 formed in the proximal end of the spinal implant 10 until the abutment tabs 87 (FIG. 10) engage the proximal end of the spinal implant 10. The undercut 89 formed in the distal portion 86 captures a portion of the lower body 30 of the implant 10 (FIG. 12B) to longitudinally fix the lower body 30 to the lower section 81 of the insertion tool 80. During insertion of the distal portion 86 into the lower body 30 of the spinal implant 10, the distal end of the spreading rod 101 remains proximal to the spinal implant 10.

With the distal portion 86 received within the proximal opening 18 of the implant 10, the thumb wheel 112 is rotated to extend the spreading rod 101 into the proximal opening 18 of the spinal implant 10. As the spreading rod 101 is extended into the proximal opening 18, the distal end of the rod guide 104 engages the angled surface 27 of the upper body 20 to secure the implant 10 to the distal portion 86 of the lower section 81.

With the implant 10 secured to the lower section 81, the implant 10 is positioned in an intervertebral space. It will be appreciated, that during insertion of the implant 10, the locking assembly 15 may be in the locked state to prevent the upper and lower bodies 20, 30 from pivoting away from one another. When the locking assembly 15 is in the locked state and the distal end of the rod guide 104 engages the angled surface 27 of the upper body 20 such that the engagement of the rod guide 104 and the upper surface 27 secures the implant 10 to the insertion tool 80.

With particular reference to FIGS. 13A and 13B, when the implant 10 is positioned within the intervertebral space and the locking assembly 15 in the unlocked state, the spreading rod 101 is translated into the longitudinal passage 18 to pivot the upper and lower bodies 20, 30 away from one another until the implant 10 has a desired height within the intervertebral space, i.e., the upper body 20 is in a desired position relative to the lower body 30. The spreading rod 101 is translated by rotating the thumb wheel 112 that threadably engages the proximal end 102 of the spreading rod 101 to extend the spreading rod 101 through the longitudinal passage 18. It will be appreciated that the ramp 104a may engage the angled surface 27 of the upper body 20 as the spreading rod 101 is extended to pivot the upper and lower bodies 20, 30 away from one another. As the upper and lower bodies 20, 30 pivots away from one another, that the biasing members 76 urge the locking pawl 50 towards the locking flange 24 such that the teeth 55 of the locking pawl 50 slide or ratchet over the teeth 25 of the locking flange 24 of the upper body 20. It will be appreciated that with the locking assembly 15 in the unlocked state, the locking pawl 50 pivots between its locked and unlocked positions as the teeth 55 ratchet over the teeth 25 of the locking flange 24.

When the implant 10 has a desired height within the intervertebral space, the locking rod 106 is used to transition the locking key 60 from the unlocked state to the locked state. When the locking key 60 is in the height of the implant 10 is fixed, i.e., the upper body 20 and the lower body 30 are secured in a desired position relative to one another. To transition the locking key 60 from the unlocked state to the locked state, the engagement end 107 of the locking rod 106 is rotated in a first radial direction out of the transport portion 95 of the locking recess 94 and into the engagement portion 96 of the locking recess 94. The engagement end 107 is moved distally through the engagement portion 96 of the locking recess 94 until the distal end 108 of the locking rod 106 engages the proximal end 61 of the locking key 60 as shown in FIG. 13A.

When the distal end 108 of the locking rod 106 engages the proximal end 61 of the locking key 60, the engagement end 107 of locking rod 106 is rotated within the locking portion 97 of the locking recess 94 to rotate the locking key 60 in the first direction such that the locking key 60 is transitioned to its locked state and the locking pawl 50 is secured in its locked position. It will be appreciated that as the locking rod 106 is rotated, the opposing ball flats 69 rotate from a vertical orientation to a horizontal orientation. It is contemplated that the rotation of the locking rod 106, and thus the locking key 60, from the unlocked state to the locked state is about 90° or a quarter turn. The keyed ring 62 of the locking key 60 engages the stop pin 72 to prevent over rotation of the locking key 60 past its locked state.

With the locking key 60 in its locked state and the implant 10 in its desired position, the locking rod 106 is disengaged from the locking key 60 by proximally moving the engagement end within the locking portion 97 of the locking recess 94. The spreading rod 101 is then withdrawn from the implant 10 by rotating the thumb wheel 112 in a second radial direction, opposite the first radial direction. When the rod guide 104 is proximal to the implant 10, the distal portion 86 of the lower section 81 is removed from the implant 10.

It will be appreciated that the if the locking rod 106 is rotated in a second radial direction, opposite the first direction, with the locking rod 106 engaged with the locking key 60, the locking key 60 transitions to the unlocked state to permit the upper body 20 and the lower body 30 to move away from one another. It will also be appreciated that the biasing members 76 urge the locking pawl 50 to the locked position to prevent the upper body 20 and the lower body 30 from moving towards one another when the locking key 60 is in the unlocked state.

Referring to FIGS. 1 and 10, a kit provided in accordance with the present disclosure includes an adjustable implant and an insertion tool. The adjustable implant of the kit may be any of the adjustable implants disclosed herein (e.g., implant 10) and the insertion tool of the kit may be any of the insertion tools disclosed herein (e.g., insertion tool 80).

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. A method of expanding an adjustable implant, the method comprising:

positioning the adjustable implant in an intervertebral space, the adjustable implant including:

a lower body;

an upper body including a locking flange extending towards the lower body;

a locking pawl secured to the lower body, the locking pawl preventing the upper body and the lower body from pivoting towards one another; and a locking key;

pivoting at least one of a distal end of the upper body and a distal end of the lower body away from the distal end of the other one of the upper and lower bodies, the locking pawl ratcheting between a locked position and an unlocked position as one of the upper body and the lower body pivots away from the other one of the upper and lower bodies; and transitioning the locking key to a locked state to fix the locking pawl in the locked position such that the upper body is fixed relative to the lower body.

2. The method according to claim 1, wherein pivoting the at least one of a distal end of the upper body and a distal end of the lower body away from the distal end of the other one of the upper and lower bodies includes inserting an insertion tool in a passage defined by the upper and lower bodies.

3. The method according to claim 2, further comprising capturing a portion of the lower body within a cutout defined in a distal portion of the insertion tool to longitudinally fix the implant relative to the insertion tool.

4. The method according to claim 2, further comprising translating a spreading rod of the insertion tool into the passage to pivot the distal end of the upper body and the distal end of the lower body away from one another.

5. The method according to claim 4, wherein translating the spreading rod of the insertion tool includes engaging the upper body with a rod guide to pivot the distal end of the upper body and the distal end of the lower body away from one another.

6. The method according to claim 5, wherein translating the spreading rod includes rotating a thumb wheel threadably coupled to a proximal end of the spreading rod.

7. The method according to claim 1, wherein transitioning the locking key to the locked state includes rotating the locking key.

8. The method according to claim 7, wherein rotating the locking key includes engaging a stop pin coupled to the locking pawl with a keyed ring of the locking key to limit rotation of the locking key.

9. The method according to claim 1, further comprising engaging the locking key with a locking rod of an insertion tool and wherein transitioning the locking key to the locked state includes rotating the locking rod to rotate the locking key.

10. The method according to claim 9, wherein engaging the locking key includes receiving a proximal end of the locking key in a recess defined in a distal end of the locking rod.

11. The method according to claim 9, wherein engaging the locking key includes rotating a proximal engagement end of the locking rod disposed within a transport portion of a locking recess defined in an upper section of the insertion tool in a first radial direction and sliding the proximal engagement end of the locking rod within an engagement portion of the locking recess until the locking rod is engaged with the locking key, the engagement portion positioned distal to the transport portion.

12. The method according to claim 11, wherein transitioning the locking key to the locked state includes rotating the locking rod within a locking portion of the locking recess in the first radial direction, the locking portion positioned distal of the engagement portion.

13. The method according to claim 12, further comprising disengaging the locking rod from the proximal end of the locking key by translating the proximal engagement portion proximally within the locking portion of the locking recess.

14. A method of pivoting at least one of an upper body and a lower body of an adjustable implant relative to one another, the method comprising:

pivoting a distal end of at least one of the upper and lower bodies away from one the distal end of the other one of the upper and lower bodies such that a locking pawl, which is in an unlocked state and pivotally secured to the lower body, ratchets against a locking flange of the upper body, the locking flange extending towards the lower body; and transitioning a locking key having a distal end that extends through the locking pawl and received in the locking flange to a locked position to fix the locking pawl in a locked state such that the upper and lower bodies are fixed relative to one another.

15. The method according to claim 14, wherein pivoting a distal end of at least one of the upper and lower bodies away from one the distal end of the other one of the upper and lower bodies includes inserting an inserter through a passage defined between proximal ends of the upper and lower bodies which are pivotally coupled to one another.

16. The method according to claim 15, further comprising capturing a portion of the lower body within a cutout defined in a distal portion of the insertion tool to longitudinally fix the implant relative to the insertion tool.

17. The method according to claim 14, wherein transitioning the locking key includes rotating the locking key such that the distal end of the locking key prevents the locking pawl from pivoting away from locking flange.

18. The method according to claim 14, further comprising engaging the locking key with a locking rod of an insertion tool, and wherein transitioning the locking key includes rotating the locking rod to affect rotation of the locking key.

19. The method according to claim 14, wherein ratcheting the locking pawl against the locking flange includes positioning a biasing member between the lower body and a biasing finger of the locking pawl to urge the locking pawl towards the locking flange.

*20. A method of expanding an adjustable implant, the method comprising:*

*positioning an adjustable implant in an intervertebral space between an upper vertebral body and a lower vertebral body spaced apart from one another in a height dimension;*

*advancing a spreader having an engagement surface along an axis within a passage between an upper body and a lower body of the adjustable implant such that the advancement of the spreader along the axis causes the engagement surface of the spreader to engage and slide along a portion of the inner surface of the adjustable implant along the passage while pushing the portion of the inner surface laterally away from the axis, to thereby spread the upper and lower bodies of the adjustable implant away from one another in the height dimension to an expanded configuration; and*

*removing the spreader from between the upper and lower bodies of the adjustable implant while maintaining the expanded configuration.*

*21. The method according to claim 20, wherein advancing the spreader along the axis comprises advancing the spreader from a proximal end of the adjustable implant towards a distal end of the adjustable implant.*

*22. The method according to claim 20, wherein spreading the upper and lower bodies away from one another comprises pivoting the upper and lower bodies away from one another.*

*23. The method according to claim 22, wherein advancing the spreader comprises advancing the spreader in a distal direction along the axis, and wherein pivoting the upper and lower bodies away from one another comprises pivoting the upper and lower bodies about a pivot axis at a proximal end of the adjustable implant.*

*24. The method according to claim 20, wherein the engagement surface of the spreader is obliquely oriented with respect to the axis.*

*25. The method according to claim 20, wherein the portion of the inner surface of the adjustable implant is obliquely oriented with respect to the axis.*

*26. The method according to claim 25, wherein the obliquely oriented portion of the inner surface is disposed in a proximal region of the adjustable implant.*

*27. The method according to claim 20, wherein maintaining the expanded configuration can be achieved at each of a plurality of different amounts of expansion, such that the spreader is removable from between the upper and lower bodies at any selected one of the amounts of expansion.*

*28. The method according to claim 27, wherein maintaining the expanded configuration includes utilizing a ratchet that permits the upper and lower bodies to move in one direction but prevents the upper and lower bodies from moving in another direction.*

*29. The method according to claim 28, further comprising locking the ratchet such that, at the selected amount of expansion, the upper and lower bodies are prevented from moving further away from one another and are also prevented from moving towards one another.*

*30. The method according to claim 20, wherein removing the spreader from between the upper and lower bodies comprises removing an implant insertion tool connected to a proximal end of the adjustable implant, the spreader being a component of the implant insertion tool.*

*31. The method according to claim 30, wherein advancing the spreader along the axis comprises advancing at least a distal end of the spreader into an opening at the proximal end of the adjustable implant.*

*32. The method according to claim 31, wherein advancing the spreader along the axis comprises advancing at least the distal end of the spreader into an open interior region of the adjustable implant.*

*33. The method according to claim 32, further comprising filling the open interior region of the adjustable implant with a bone growth facilitator material.*

* * * * *